(12) United States Patent
O'Bryan et al.

(10) Patent No.: US 12,121,407 B2
(45) Date of Patent: Oct. 22, 2024

(54) VEIN MAPPING DEVICES, SYSTEMS, AND METHODS

(71) Applicant: Becton, Dickinson and Company, Franklin Lakes, NJ (US)

(72) Inventors: Jeffrey C. O'Bryan, Murray, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 460 days.

(21) Appl. No.: 17/110,907

(22) Filed: Dec. 3, 2020

(65) Prior Publication Data

US 2021/0186649 A1 Jun. 24, 2021

Related U.S. Application Data

(60) Provisional application No. 62/949,893, filed on Dec. 18, 2019.

(51) Int. Cl.
*A61B 90/00* (2016.01)
*A61B 5/00* (2006.01)
(Continued)

(52) U.S. Cl.
CPC .............. *A61B 90/39* (2016.02); *A61B 5/489* (2013.01); *A61B 8/08* (2013.01); *A61B 8/488* (2013.01);
(Continued)

(58) Field of Classification Search
CPC ........... A61B 90/39; A61B 5/489; A61B 8/08; A61B 8/488; A61B 2090/395; A61B 2090/3937; A61B 8/462; A61B 8/0891; A61B 5/0071; A61B 5/0095; A61B 5/055; A61B 6/504; A61B 8/085;
(Continued)

(56) References Cited

U.S. PATENT DOCUMENTS

| 2009/0163809 A1* | 6/2009 | Kane ...................... A61B 90/36 600/443 |
| 2012/0211006 A1* | 8/2012 | Gill ........................ A61B 34/30 128/200.26 |

(Continued)

FOREIGN PATENT DOCUMENTS

| IL | 240549 A | 2/2019 |
| JP | 2016179053 | 10/2016 |

(Continued)

*Primary Examiner* — Baisakhi Roy
*Assistant Examiner* — Kaitlyn E Sebastian
(74) *Attorney, Agent, or Firm* — Kirton McConkie; Whitney Blair; Kevin Stinger (57) ABSTRACT

A device, system, and method for printing a vein map onto a patient's skin may include a probe and a printer. The probe may be configured to identify a location of a target vein beneath the patient's skin. The printer may be configured to receive the location and, using the location, print the vein map onto the patient's skin to indicate the location. The vein map may comprise antimicrobial ink printed onto the patient's skin with one or more colors and/or one or more patterns. The vein map may be a two-dimensional vein map or a three-dimensional vein map that indicates the location of the target vein within the patient, a width of the target vein, and/or a depth of the target vein within the patient.

7 Claims, 6 Drawing Sheets

(51) Int. Cl.
- *A61B 8/08* (2006.01)
- *B41J 3/407* (2006.01)
- *B41M 5/00* (2006.01)
- *C09D 11/03* (2014.01)

(52) U.S. Cl.
CPC .......... *B41J 3/4073* (2013.01); *B41M 5/0047* (2013.01); *B41M 5/0076* (2013.01); *C09D 11/03* (2013.01); *A61B 2090/395* (2016.02)

(58) Field of Classification Search
CPC ..... A61B 2090/3904; A61B 2090/3983; B41J 3/4073; B41J 3/36; B41M 5/0047; B41M 5/0076; C09D 11/03

See application file for complete search history.

(56) References Cited

U.S. PATENT DOCUMENTS

| | | | | |
|---|---|---|---|---|
| 2014/0236019 A1* | 8/2014 | Rahum | ................ | A61B 5/0075 600/473 |
| 2020/0085529 A1* | 3/2020 | Luo | ........................ | A61B 90/39 |

FOREIGN PATENT DOCUMENTS

| | | | | |
|---|---|---|---|---|
| WO | 2005120193 | A2 | 12/2005 | |
| WO | 2010029521 | A2 | 3/2010 | |
| WO | WO-2013150549 | A2 * | 10/2013 | ........... A61B 5/0059 |
| WO | 2014125492 | A1 | 8/2014 | |

\* cited by examiner

VEIN MAPPING DEVICES, SYSTEMS, AND METHODS

RELATED APPLICATIONS

This application claims the benefit of U.S. Provisional Application No. 62/949,893, filed Dec. 18, 2019, and entitled VEIN MAPPING DEVICES, SYSTEMS, AND METHODS, which is incorporated herein in its entirety.

BACKGROUND

Catheters are commonly used for a variety of infusion therapies. For example, catheters may be used for infusing fluids into a patient such as saline solution, medication, total parenteral nutrition, etc. Catheters may also be used for withdrawing blood from the patient.

A common type of catheter is an over-the-needle peripheral intravenous catheter ("PIVC"). Other common types of catheters include, but are not limited to, peripherally inserted central catheters ("PICC"), central venous catheters ("CVC"), etc.

As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are typically inserted at a shallow angle through the skin and into a blood vessel of the patient, such as an artery, a vein, or other vasculature of the patient. Once the PIVC has been properly placed within the blood vessel, the introducer needle may be withdrawn and the PIVC may be secured within the blood vessel by securing a catheter adapter (coupled with the PIVC) to the skin of the patient with dressing.

The insertion success rate for a PIVC is about 70% for adult patients and less than 50% for pediatric patients. One of the main challenges to successful insertion is correctly identifying and locating a suitable target vein within the patient. For example, non-superficial/deep veins may be difficult for a clinician to locate within a patient and then target for catheter insertion utilizing existing catheter insertion techniques. Accordingly, improved devices, systems, and methods for identifying a location of a target vein within a patient would be desirable.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to devices, systems, and methods for identifying a location of a vein in a patient. The various devices, systems, and methods of the present disclosure have been developed in response to the present state of the art, and in particular, in response to the problems and needs in the art that have not yet been fully solved by currently available devices, systems, and methods for identifying a location of a vein within a patient to facilitate insertion of a catheter into the vein.

In some embodiments, an apparatus for printing a vein map onto a patient's skin may include an ultrasonic probe and a print head. The ultrasonic probe may be configured to identify a location of a target vein beneath the patient's skin via ultrasound. The print head may be coupled to the ultrasonic probe and configured to: (1) receive the location; and (2) using the location, print the vein map onto the patient's skin above the location such that the vein map indicates the location of the target vein within the patient.

In some embodiments of the apparatus, the vein map may include a two-dimensional vein map that indicates the location of the target vein within the patient below the vein map, and a width of the target vein.

In some embodiments of the apparatus, the vein map may include a three-dimensional vein map that indicates the location of the target vein within the patient below the vein map, a width of the target vein, and a depth of the target vein within the patient.

In some embodiments of the apparatus, the three-dimensional vein map may include one or more colors that indicate one or more depths of the target vein within the patient.

In some embodiments of the apparatus, the three-dimensional vein map may include one or more patterns that indicate one or more depths of the target vein within the patient.

In some embodiments of the apparatus, the vein map may further indicate a second location for a second target vein beneath the patient's skin.

In some embodiments, a system for printing a vein map onto a patient's skin may include a probe and a printer. The probe may be configured to identify a location of a target vein beneath the patient's skin. The printer may be configured to receive the location and, using the location, print the vein map onto the patient's skin to indicate the location.

In some embodiments of the system, the vein map may include a two-dimensional vein map that indicates the location of the target vein within the patient below the vein map, and a width of the target vein.

In some embodiments of the system, the vein map may include a three-dimensional vein map that indicates the location of the target vein within the patient below the vein map, a width of the target vein, and a depth of the target vein within the patient.

In some embodiments of the system, the three-dimensional vein map may include one or more colors that indicate one or more depths of the target vein within the patient.

In some embodiments of the system, the three-dimensional vein map may include a first color that indicates a superficial target vein and a second color that indicates a deep target vein.

In some embodiments of the system, the three-dimensional vein map may include one or more patterns that indicate one or more depths of the target vein within the patient.

In some embodiments of the system, the probe may identify the location of the target vein through use of an imaging technique that may include at least one of: ultrasound, MRI, NIR, FNIR, X-rays, radiography, fluoroscopy, elastography, photoacoustic imaging, tomography, and nuclear imaging.

In some embodiments of the system, the probe may include an ultrasonic probe that utilizes the Doppler effect to identify the location of the target vein and differentiate the target vein from an artery.

In some embodiments of the system, the ultrasonic probe may be automated to scan over the patient's skin and identify the location of the target vein, and the printer may be automated to receive the location and print an automated vein map onto the patient's skin to indicate the location.

In some embodiments, a method for printing a vein map onto a patient's skin may include identifying a location of a target vein below the patient's skin with a probe, and printing a vein map onto the patient's skin that indicates the location of the target vein within the patient.

In some embodiments, the method may further include: performing an initial scan of the patient's skin with an ultrasonic probe to identify the location of the target vein; performing a subsequent scan of the patient's skin with the ultrasonic probe to verify the location of the target vein; and printing the vein map onto the patient's skin during the subsequent scan with a print head coupled to the ultrasonic probe that is configured to receive the location.

In some embodiments, the method may further include performing a scan of the patient with the probe to identify the location of the target vein below the patient's skin, and printing the vein map onto the patient's skin with a printer that is configured to receive the location and print the vein map onto the patient's skin.

In some embodiments of the method, the vein map may include at least one of: a two-dimensional vein map that indicates the location of the target vein within the patient below the vein map and a width of the target vein; and a three-dimensional vein map that indicates the location of the target vein within the patient below the vein map, a width of the target vein, and a depth of the target vein within the patient.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the spirit or scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1:
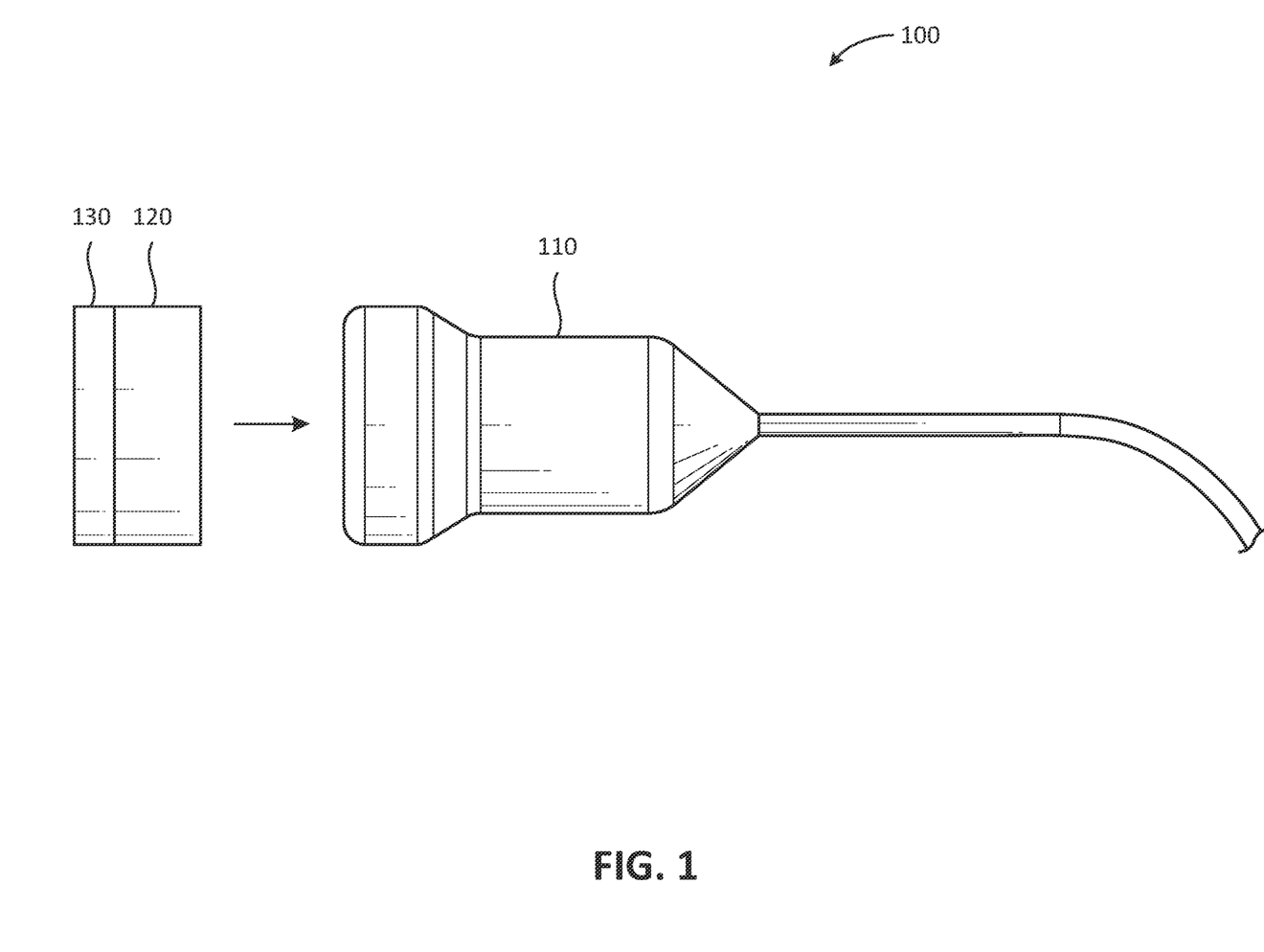
FIG. 1 illustrates an example probe that may be utilized to identify a location of a target vein beneath a patient's skin, according to some embodiments.

FIG. 1 illustrates a probe 100 that may be configured to identify a location of a target vein beneath a patient's skin. In some embodiments, the probe 100 may include an ultrasonic probe configured to: (1) identify the location of the target vein beneath the patient's skin via ultrasound; and (2) using the location, print a vein map onto the patient's skin above the location such that the vein map indicates the location of the target vein within the patient.

As defined herein, a vein map may include any marking or indicia (e.g., a line, dot, arrow, pattern, color, etc.) that may be placed on a patient to indicate a location, a width, and/or a depth of at least one target vein within the patient. In this manner, the vein map may help guide a clinician during catheter insertion, as will be discussed below in more detail with respect to FIGS. 2-5.

In some embodiments, the ultrasonic probe may generally include a probe body 110, an ultrasonic transducer 120, and a print head 130. In some embodiments, the ultrasonic transducer 120 and/or the print head 130 may each be removably couplable to the probe body 110 and/or to each other, as shown in FIG. 1. However, in other embodiments, the ultrasonic transducer 120 and/or the print head 130 may each be integrated with the probe body 110 and/or with each other. The ultrasonic transducer 120 may utilize ultrasound in conjunction with the Doppler effect to identify the location of the target vein and/or to differentiate the target vein from other veins, arteries, tissues, etc., within the patient. In some embodiments, the ultrasonic probe may be utilized to perform an initial scan of a target insertion site on the patient (e.g., an arm, a leg, a hand, a torso, etc., of the patient) in order to identify one or more target veins for catheter insertion. Once a target vein has been identified at the target insertion site, the ultrasonic probe may be moved over the target insertion site in a subsequent scan and the ultrasonic transducer 120 may verify and send the location of the target vein to the print head 130 for printing a vein map onto the patient's skin while the ultrasonic probe is moved over the target insertion during the subsequent scan.

In some embodiments, a system for printing a vein map onto a patient's skin may include the probe 100 and a printer (not shown), which may be separate from the probe 100. The probe 100 may be configured to identify the location of the target vein beneath the patient's skin. The printer may be configured to receive the location and, using the location, print a vein map onto the patient's skin to indicate the location of the target vein. The probe 100 may identify the location of the target vein through the use of any suitable medical imaging technique known in the art including, but not limited to: ultrasound, MRI, NIR, FNIR, X-rays, radiography, fluoroscopy, elastography, photoacoustic imaging, tomography, nuclear imaging, etc.

In some embodiments, a system for printing a vein map onto a patient's skin may include an automated vein mapping machine (not shown). The automated vein mapping machine may include a receptacle to receive an anatomical region of the patient (e.g., an arm, a leg, a hand, a torso, etc., of the patient). For example, an arm of the patient may be received within the receptacle and/or restrained at one or more locations within the automated vein mapping machine. A movable probe may be automated to scan over the patient's arm to identify one or more target veins within the patient's arm. An image of the one or more target veins may be stored in the automated vein mapping machine and/or sent to the printer. A printer may be automated to move over the patient's arm to print out a vein map onto the skin of the patient that indicates the location(s) of the one or more target veins.

In some embodiments, the probe 100 may include an ultrasonic probe that utilizes the Doppler effect to identify the location of the target vein and/or to differentiate the target vein from other veins, arteries, tissues, etc.

In some embodiments, the ultrasonic probe may be automated to scan over the patient's skin and identify the location of the target vein. The printer may also be automated to receive the location from the ultrasonic probe and print an automated vein map onto the patient's skin in order to indicate the location of the target vein.

Figure 2:
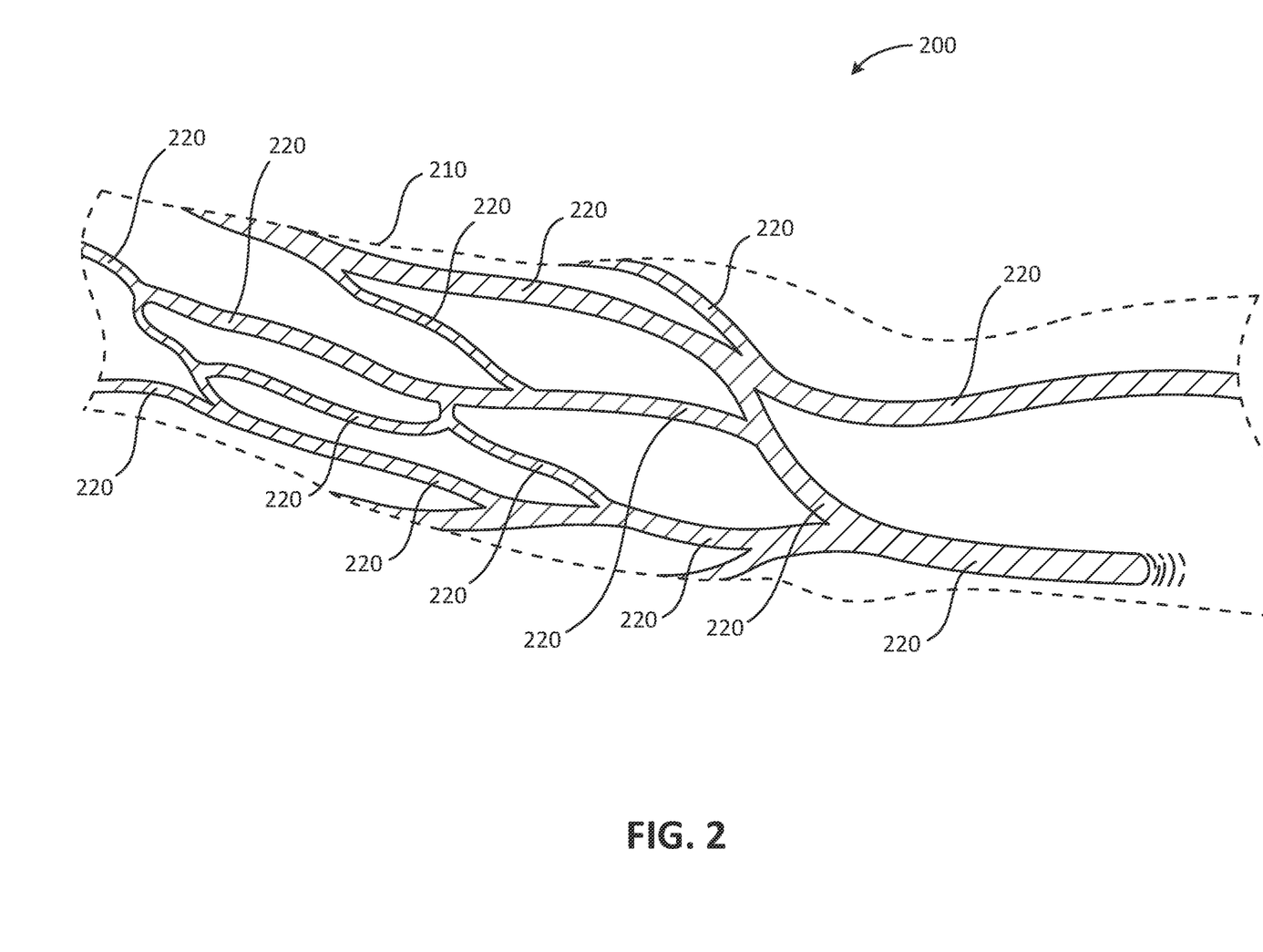
FIG. 2 illustrates an arm of a patient with an example two-dimensional vein map printed onto the patient's skin, according to some embodiments.
Figure 3:
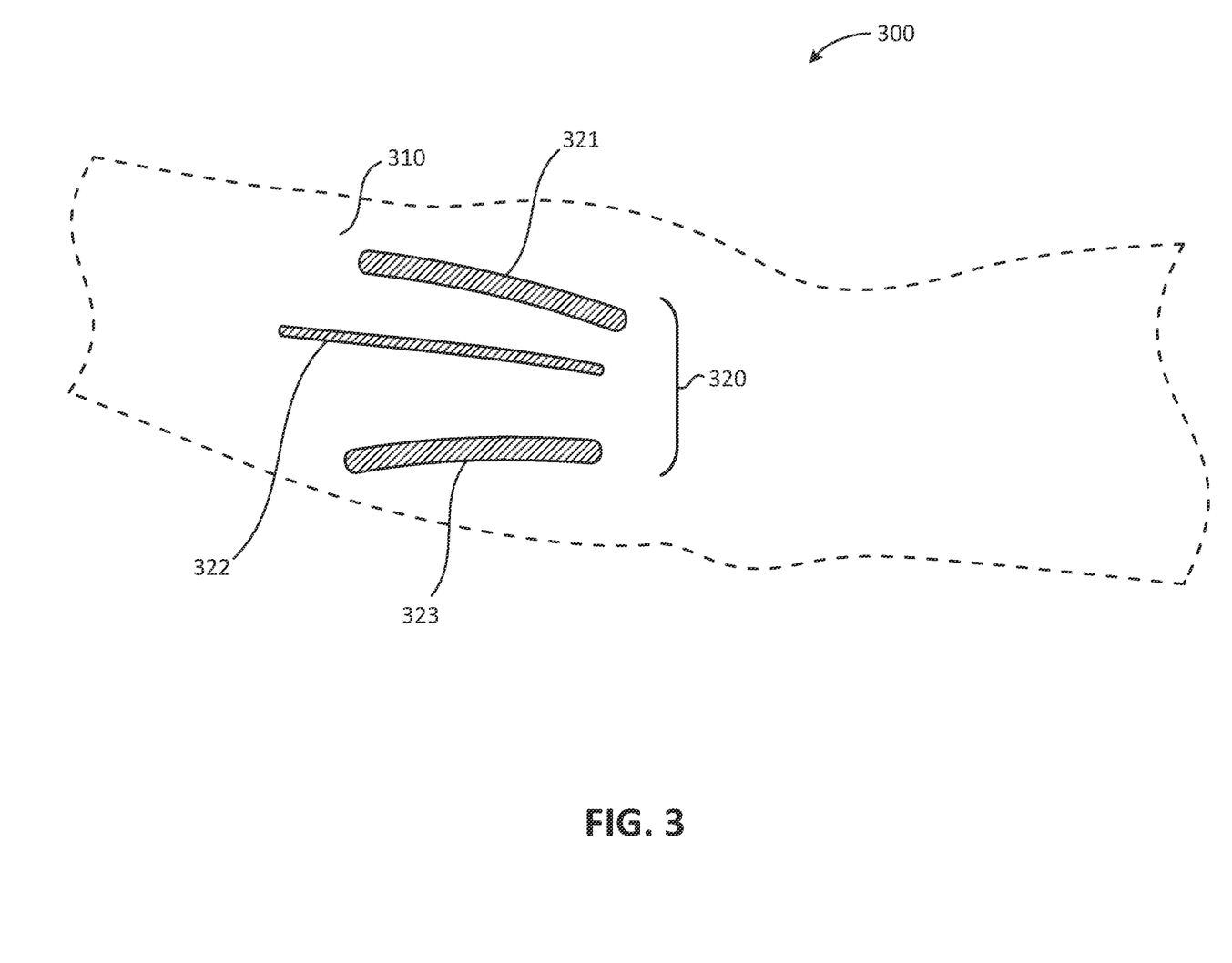
FIG. 3 illustrates an arm of a patient with an example partial two-dimensional vein map printed onto the patient's skin, according to some embodiments.
Figure 4:
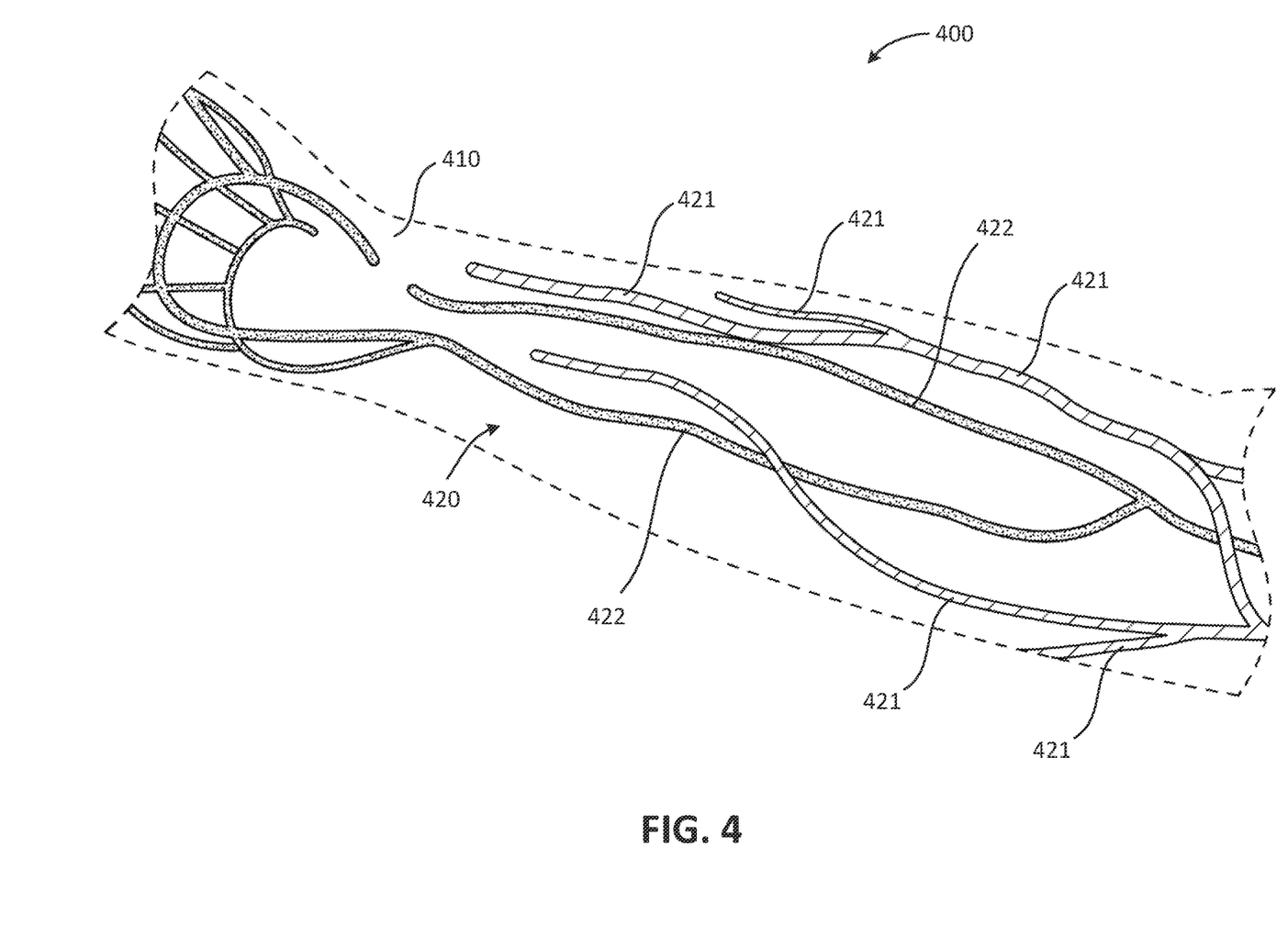
FIG. 4 illustrates an arm of a patient with an example three-dimensional vein map printed onto the patient's skin, according to some embodiments.
Figure 5:
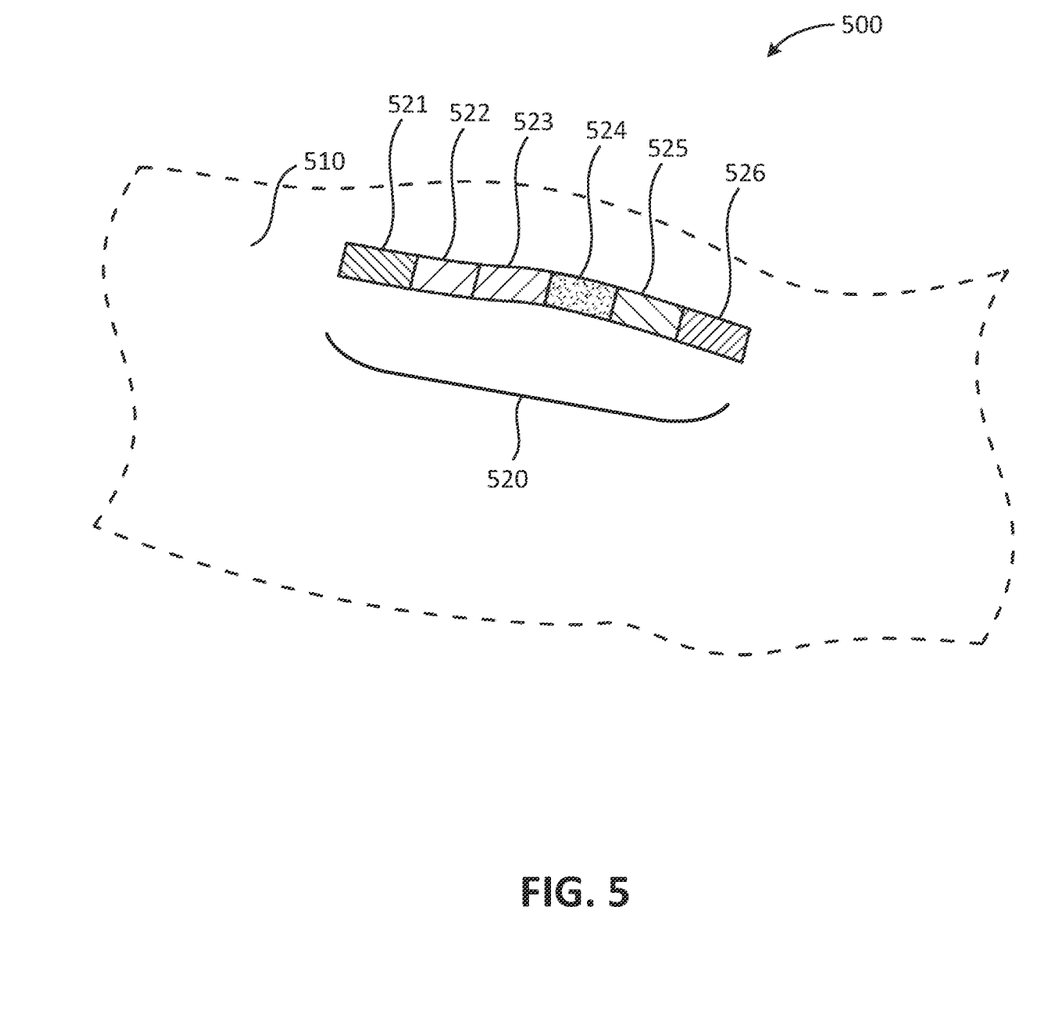
FIG. 5 illustrates an arm of a patient with an example partial three-dimensional vein map printed onto the patient's skin, according to some embodiments.

FIGS. 2-5 illustrate various example vein maps that have been printed onto an arm of a patient. In some embodiments, the vein maps can represent an entire scanned area, one or more machine-determined insertion sites, or one or more insertion sites selected by a clinician. Specifically, FIG. 2 shows a two-dimensional vein map 220 printed onto the skin 210 of the patient's arm 200; FIG. 3 shows a partial two-dimensional vein map 320 printed onto the skin 310 of the patient's arm 300; FIG. 4 shows a three-dimensional vein map 420 printed onto the skin 410 of the patient's arm 400; and FIG. 5 shows a partial three-dimensional vein map 520 printed onto the skin 510 of the patient's arm 500.

In some embodiments, a two-dimensional vein map 220 that is comprehensive may be printed onto skin 210 of the patient, is shown in FIG. 2. In this manner, a clinician can visualize most or all of the patient's veins at the target insertion site and may then select a target vein for catheter insertion.

In some embodiments, the two-dimensional vein map 220 (or any other vein map described herein) may indicate the location of the target vein within the patient below the vein map, as well as a width of the target vein. For example, the width of the target vein may be directly reflected in the width of the printed vein on the patient's skin. Moreover, the location of the target vein within the patient may lie directly below the printed vein on the patient's skin. However, it will also be understood that any other suitable technique may be utilized to indicate a location and/or a width of a target vein. For example, a location of a target vein may be indicated by arrows or other indicia on the patient's skin that may or may not lie directly above a target vein, but may be offset from the target vein. This may be desirable if the skin directly above the target vein moves a lot or otherwise is not suitable for printing. Likewise, a width of a target vein may not be directly reflected in a width of a printed vein on the patient's skin, but may be indicated by other suitable indicia printed onto the patient's skin.

In some embodiments, the two-dimensional vein map 220 (or any other vein map described herein) may indicate a plurality of locations for a plurality of target veins beneath the patient's skin.

In some embodiments, the two-dimensional vein map 220 (or any other vein map described herein) may include an antimicrobial ink printed onto the patient's skin.

In some embodiments, the antimicrobial ink of the two-dimensional vein map 220 (or any other vein map described herein) may not be directly printed onto the patient's skin. For example, the antimicrobial ink may be printed onto other tissues of the patient, or onto a material that covers the patient (e.g., a bandage, a fluid, a gel, etc., covering the target insertion site of the patient).

In some embodiments, a partial two-dimensional vein map 320 may be printed onto the skin 310 of the patient, as shown in FIG. 3. In this manner, a clinician can visualize one or more recommended target veins at a target insertion site and select a target vein for catheter insertion. A first target vein 321, a second target vein 322, and a third target vein 323 are shown in the partial two-dimensional vein map 320 of FIG. 3. However, it will be understood that any of the vein maps described herein may include any number of target veins.

In some embodiments, a three-dimensional vein map 420 may be printed onto the skin 410 of the patient, as shown in FIG. 4. In this manner, a clinician can visualize one or more target veins at one or more locations and depths within the patient and select a target vein for catheter insertion. A first target vein 421 at a first depth and a second target vein 422 at a second depth are shown in FIG. 4. However, it will be understood that any number of target veins at any number of depths may be represented within the vein maps of the present disclosure.

In some embodiments, one or more colors may be incorporated into the three-dimensional vein maps of the present disclosure to represent one or more depths of target veins within the patient. For example, in some embodiments a first color may indicate a superficial target vein and a second color may indicate a deep target vein (e.g., see FIG. 4).

In some embodiments, one or more patterns may be incorporated into the three-dimensional vein maps of the present disclosure to represent one or more depths of target veins within the patient. For example, in some embodiments a first pattern (e.g., dots, etc.) may indicate a superficial target vein, and a second pattern (e.g., lines, etc.) may indicate a deep target vein (e.g., see FIG. 4).

In some embodiments, a partial three-dimensional vein map 520 may be printed onto the skin 510 of the patient, as shown in FIG. 5. In this example, a clinician can visualize a target vein as its depth varies within the patient at different locations. FIG. 5 shows how the depth of the target vein can vary within the patient at a first location having a first depth 521, a second location having a second depth 522, a third location having a third depth 523, a fourth location having a fourth depth 524, a fifth location having a fifth depth 525, and a sixth location having a sixth depth 526. Each of these depths may be represented by a different color and/or pattern printed onto the patient's skin, as described above. Each of these colors and/or patterns may also correspond to different depth values and/or different depth ranges (e.g., 2-5 mm for the first depth 521, 5-8 mm for the second depth 522, etc.). In this manner, the printed vein maps of the present disclosure can be color coded and/or pattern coded to indicate one or more depths for one or more target veins. The color/pattern coding scheme can be simple (e.g., two tones/patterns for superficial and deep veins, as shown in FIG. 4)

or consist of more colors/patterns to provide better depth resolution (e.g., see FIG. 5). It will also be understood that any characteristic of any vein map described herein may be mixed and matched with any other vein map that is described herein. For example, the different depth patterns/colors of FIGS. 4 and 5 may be incorporated into the vein maps of FIGS. 2 and 3, etc.

Figure 6:
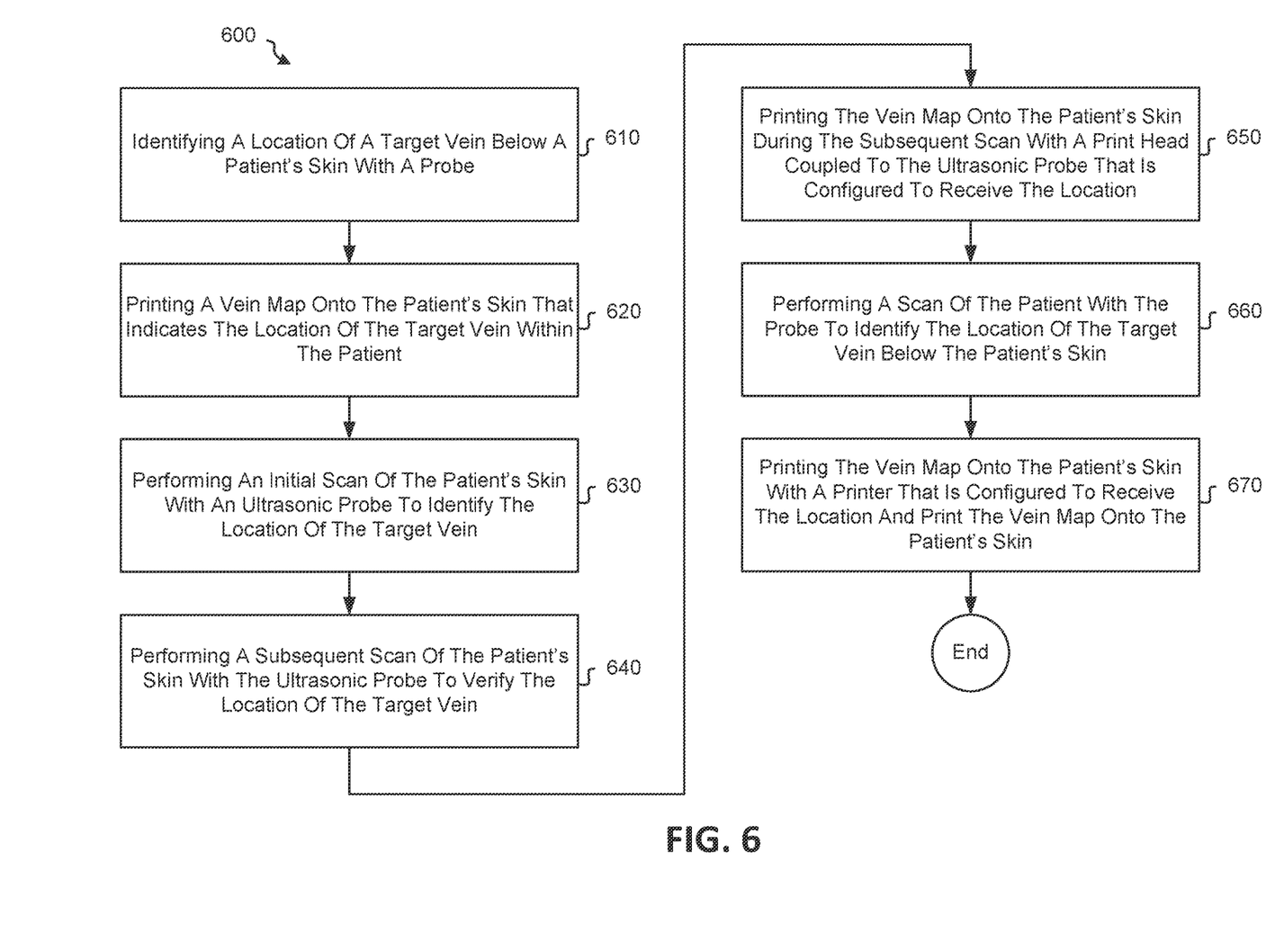
FIG. 6 illustrates a flow chart of a method for printing a vein map onto a patient's skin, according to some embodiments.

FIG. 6 illustrates a flow chart of a method 600 for printing a vein map onto a patient's skin, according to some embodiments. The method may begin with a step 610 in which a location of a target vein may be identified below the patient's skin with a probe. The probe may identify the location of the target vein through the use of any suitable medical imaging technique known in the art including, but not limited to ultrasound, MRI, NIR, FNIR, X-rays, radiography, fluoroscopy, elastography, photoacoustic imaging, tomography, nuclear imaging, etc.

Once the location of the target vein has been identified below the patient's skin with the probe, the method 600 may proceed to a step 620 in which a vein map may be printed onto the patient's skin to indicate the location of the target vein within the patient, and the method 600 may end. As discussed above, the vein map may include any marking or indicia (e.g., a line, dot, arrow, pattern, color, etc.) that may be placed on a patient to indicate a location, a width, and/or a depth of at least one target vein within the patient. In this manner, the vein map may help guide a clinician during catheter insertion.

Alternatively, or in addition thereto, the method 600 may proceed to steps 630, 640, and/or 650, in at least some embodiments. In the step 630, an initial scan of the patient's skin may be performed with an ultrasonic probe to identify the location of the target vein.

Once the initial scan of the patient's skin has been performed with the ultrasonic probe to identify the location of the target vein, the method 600 may proceed to steps 640 and/or 650 in which a subsequent scan of the patient's skin may be performed with the ultrasonic probe to verify the location of the target vein, and the vein map may be printed onto the patient's skin during the subsequent scan with a print head coupled to the ultrasonic probe that is configured to receive the location, and the method 600 may end.

Alternatively, or in addition thereto, the method 600 may proceed to steps 660 and/or 670, in at least some embodiments. In the step 660, a scan of the patient may be performed with the probe to identify the location of the target vein below the patient's skin.

Once the scan of the patient has been performed with the probe to identify the location of the target vein below the patient's skin, the method 600 may proceed to step 670 in which the vein map may be printed onto the patient's skin with a printer that is configured to receive the location and print the vein map onto the patient's skin, and the method 600 may end.

Any methods disclosed herein include one or more steps or actions for performing the described method. One or more of the method steps and/or actions may be omitted from any of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or −10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. An apparatus for printing a vein map onto a patient's skin comprising:
    a probe body;
    an ultrasonic transducer configured to identify a location of a target vein beneath the patient's skin via ultrasound; and
    a print head coupled to the ultrasonic transducer and configured to:
        receive the location; and
        using the location, print the vein map onto the patient's skin above the location such that the vein map indicates the location of the target vein within the patient,
    wherein the ultrasonic transducer and the print head are removably coupled to the probe body, the print head being immediately adjacent and distal to the ultrasonic transducer.

2. The apparatus of claim 1, wherein the vein map comprises a two-dimensional vein map that indicates:
    the location of the target vein within the patient below the vein map; and
    a width of the target vein.

3. The apparatus of claim 1, wherein the vein map comprises a three-dimensional vein map that indicates:
    the location of the target vein within the patient below the vein map;
    a width of the target vein; and
    a depth of the target vein within the patient.

4. The apparatus of claim 3, wherein the three-dimensional vein map comprises one or more colors that indicate one or more depths of the target vein within the patient.

5. The apparatus of claim 3, wherein the three-dimensional vein map comprises one or more patterns that indicate one or more depths of the target vein within the patient.

6. The apparatus of claim 1, wherein the vein map comprises an antimicrobial ink printed onto the patient's skin.

7. The apparatus of claim 1, wherein the vein map further indicates a second location for a second target vein beneath the patient's skin.

* * * * *